United States Patent
Diaz-Arias et al.

(10) Patent No.: US 11,482,048 B1
(45) Date of Patent: Oct. 25, 2022

(54) METHODS AND APPARATUS FOR HUMAN POSE ESTIMATION FROM IMAGES USING DYNAMIC MULTI-HEADED CONVOLUTIONAL ATTENTION

(71) Applicant: INSEER Inc., Iowa City, IA (US)

(72) Inventors: Aiec Diaz-Arias, Columbia, MO (US); Dmitriy Shin, Columbia, MO (US); Jean E. Robillard, Iowa City, IA (US); Mitchell Messmore, Iowa City, IA (US); John Rachid, Iowa City, IA (US)

(73) Assignee: INSEER Inc., Iowa City, IA (US)

( * ) Notice: Subject to any disclaimer, the term of this patent is extended or adjusted under 35 U.S.C. 154(b) by 0 days.

(21) Appl. No.: 17/740,650

(22) Filed: May 10, 2022

(51) Int. Cl.
| | |
|---|---|
| *G06K 9/00* | (2022.01) |
| *G06V 40/20* | (2022.01) |
| *G16H 20/30* | (2018.01) |
| *G06V 10/80* | (2022.01) |
| *G06V 40/10* | (2022.01) |

(52) U.S. Cl.
CPC ............ *G06V 40/23* (2022.01); *G06V 10/806* (2022.01); *G06V 40/103* (2022.01); *G16H 20/30* (2018.01)

(58) Field of Classification Search
CPC .... G06V 40/23; G06V 10/806; G06V 40/103; G16H 20/30
See application file for complete search history.

(56) References Cited

U.S. PATENT DOCUMENTS

| | | | | |
|---|---|---|---|---|
| 10,776,423 | B2 * | 9/2020 | Kontschieder | G06K 9/6278 |
| 10,830,584 | B2 * | 11/2020 | Boulkenafed | G06V 10/811 |
| 2019/0012530 | A1 * | 1/2019 | Tomono | G06T 7/251 |

FOREIGN PATENT DOCUMENTS

WO    WO-2020232069 A1 *  11/2020  .............. G06K 9/00

OTHER PUBLICATIONS

Karpathy, A. et al., "Large-scale Video Classification with Convolutional Neural Networks," [Online], Retrieved from the Internet: https://www.cv-foundation.org/openaccess/content_cvpr_2014/papers/Karpathy_Large-scale_Video_Classification_2014_CVPR_paper.pdf, CVPR (2014), 8 pages.

Zheng, C. et al., "3D Human Pose Estimation with Spatial and Temporal Transformers," [Online], Retrieved from the Internet: https://openaccess.thecvf.com/content/ICCV2021/papers/Zheng_3D_Human_Pose_Estimation_With_Spatial_and_Temporal_Transformers_ICCV_2021_paper.pdf, ICCV (2021), 10 pages.

Zhou, B. et al., "Learning Deep Features for Discriminative Localization," [Online], Retrieved from the Internet: https://openaccess.thecvf.com/content_cvpr_2016/papers/Zhou_Learning_Deep_Features_CVPR_2016_paper.pdf, CVPR (2016), 9 pages.

* cited by examiner

*Primary Examiner* — Dhaval V Patel
(74) *Attorney, Agent, or Firm* — Cooley LLP

(57) ABSTRACT

An apparatus for 3D human pose estimation using dynamic multi-headed convolutional attention mechanism is presented. The apparatus contains two dynamic multi-headed convolutional attention mechanism with spatial attention and another with temporal attention that leverages the spatial attention mechanism to extract frame-wise inter-joint dependencies by analyzing sections of limbs that are related. The temporal attention mechanism extracts global inter-frame relationships by analyzing correlations between the temporal profile of joints. The temporal profile mechanism leads to a more diverse temporal attention map while achieving substantial parameter reduction.

20 Claims, 5 Drawing Sheets

METHODS AND APPARATUS FOR HUMAN POSE ESTIMATION FROM IMAGES USING DYNAMIC MULTI-HEADED CONVOLUTIONAL ATTENTION

FIELD

The present disclosure relates to the field of artificial intelligence, specifically to methods and apparatus for human pose estimation using dynamic multi-headed convolutional attention based on images and/or videos collected from a sensor(s) such as a camera.

BACKGROUND

Artificial intelligence and image processing enables computers to reproduce three-dimensional (3D) skeletal representations of humans based on images and/or video collected from a camera. By leveraging deep neural networks for 3D human pose estimation, image processors can learn mappings from red-green-blue (RGB) images to 3D skeletal representations. Deep neural networks can also use an input containing two-dimensional frames of a human subject to identify specific joints and interconnecting limbs to produce such 3D skeletal representations. Current 3D human pose estimators, however, typically suffer substantial computational overhead and simultaneously poor generalizability due to capturing motion in staged environments. Furthermore, current implementations of deep neural networks attempt to solve such issues with superfluous hidden layers and overcomplicate the mapping of spatial and temporal parameters. Therefore, excess noise resulting from such overcomplication can disrupt the overall smoothness of a 3D skeletal representation.

SUMMARY OF THE DISCLOSURE

In some embodiments, an apparatus is for a human pose estimation. The apparatus includes a processor and a memory operatively connected to the processor. The memory contains instructions configuring the processor to receive image frames, each image frame from the plurality of image frames containing a measured temporal joint data of a subject. The memory further stores instructions causing the processor to train a limb segment machine-learning model of machine-learning models using an interrelation training set that contains a limb segment image data correlated to a limb matrix in a motion sequence. The memory further stores instructions causing the processor to execute the limb segment machine-learning model to identify frame interrelations using the plurality of image frames as an input and generate a temporal joints profile based on the plurality of frame interrelation In some embodiments, a non-transitory, processor-readable medium causes the processor to receive, from a sensor operatively coupled to the processor, a plurality of image frames containing a measured temporal joint data of a subject across at least two frames of image data from the sensor and compute a plurality of averaged convoluted quantitative identifiers based on the plurality of image frames. The non-transitory, processor-readable medium also causes the processor to train a multi-headed temporal profile machine-learning model of a plurality of machine-learning models using a temporal joints training set that includes a concatenated temporal profile correlated to a concatenated temporal sequence, execute the multi-headed temporal profile machine-learning model to output a plurality of temporal joints interrelations using the plurality of averaged convoluted quantitative identifiers as an input, and generate an aggregated temporal joints profile based on the temporal joints interrelations.

BRIEF DESCRIPTION OF THE DRAWINGS

For the purpose of illustrating the disclosure, the drawings show aspects of one or more embodiments. It should be understood, however, that the present disclosure is not limited to the precise arrangements and instrumentalities shown in the drawings.

Figure 1:
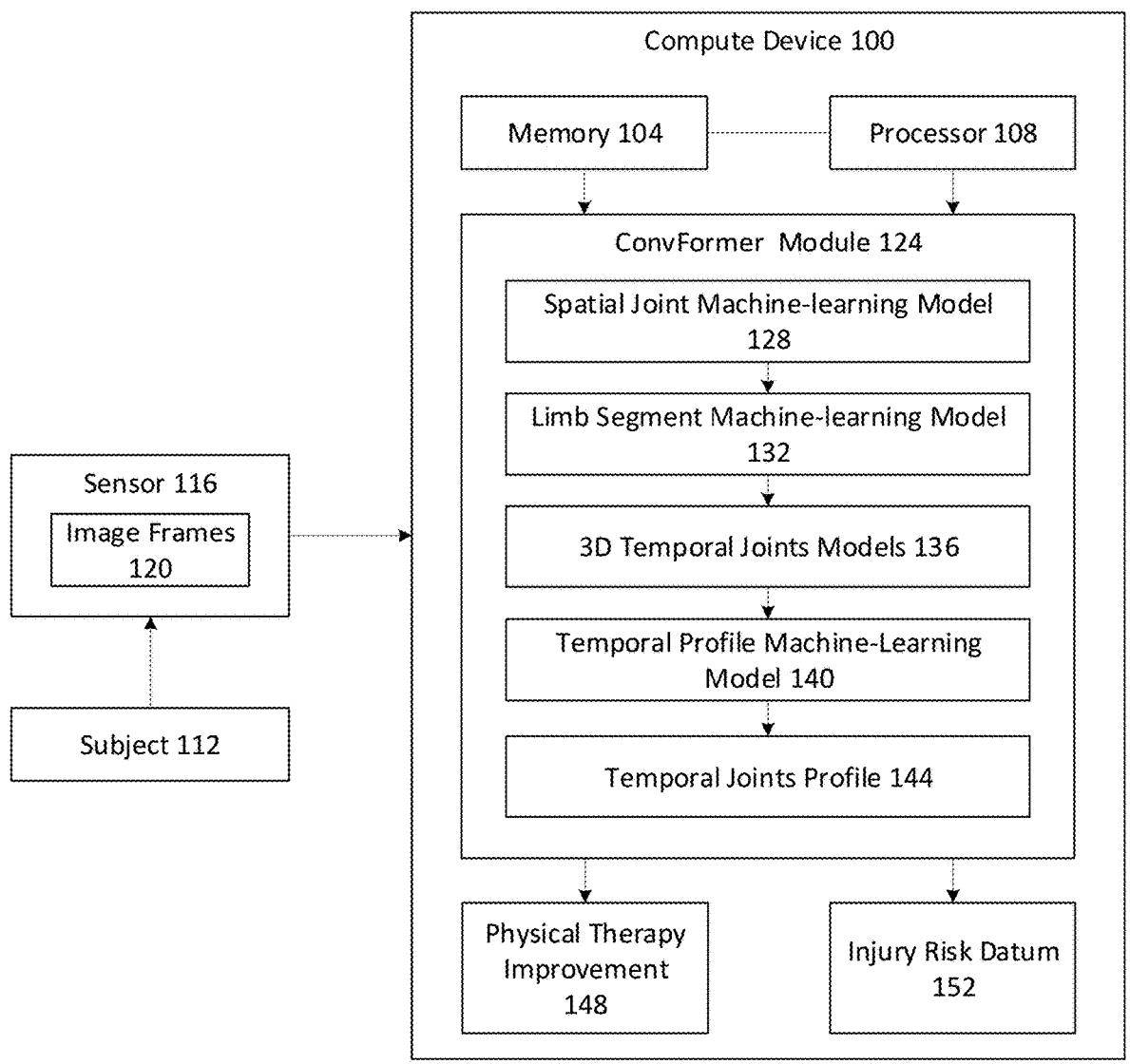
FIG. 1 is a block diagram illustrating an embodiment of a non-transient computer readable medium for producing a temporal joints profile, according to an embodiment.

The drawings are not necessarily to scale and can be illustrated by phantom lines, diagrammatic representations and fragmentary views. In certain instances, details that are not necessary for an understanding of the embodiments or that render other details difficult to perceive can have been omitted

DETAILED DESCRIPTION

In some embodiments, an apparatus is for human pose estimation using dynamic multi-headed convolutional attention. The apparatus includes a transformer called ConvFormer that leverages a dynamic convolutional multi-headed attention mechanism. In one or more embodiments, a compute device incorporating the ConvFormer can receive a two-dimensional (2D) input such as a video and/or image frames representing a human subject. The ConvFormer can convert the 2D input into a 3D skeletal representation and produce a temporal joints profile, representing a sequence of 3D poses highlighting the movement of a joint of the 3D skeleton in a temporal input. For instance, the ConvFormer receives the 2D input of a human subject and produces an image of a skeletal outline following the joints and limbs of the human subject, which can be overlayed on the original input, thereby producing an outline of the human subject's skeletal framework on top of the human subject in the 2D input. This is so, at least in part, to identify the human subject's pose and/or movement in a sequence of time. The ConvFormer can also produce a 3D skeletal representation based on the 2D input and the skeletal outline to estimate the skeletal outline's movement and position in three dimensions. As the 2D input can include a video stream containing individual image frames, the ConvFormer produces the 3D skeletal representations outlining the human subject in each frame found in the video stream. In estimating the poses of the human subject from each 3D skeletal representation on each frame, the ConvFormer can also reduce complexity between frames from using convolution based on a convolution filter size.

In some embodiments, the ConvFormer can also be used, for example, to reproduce a spatially and temporally smooth 3D skeletal representation of a human subject from the reduced sparsity. In one or more embodiments, the ConvFormer can produce temporal joints profile for each joint of a human subject and query each of those temporal joints profiles to produce a complete temporal joints profile for the overall human subject that is being analyzed by the ConvFormer. In one or more embodiments, the compute device can generate multiple layers of queries, keys, and values for each joint to produce a 3D skeletal representation and a 3D joint(s) sequential model denoted by a temporal joints profile. For instance, the ConvFormer can generate the queries, keys, and values from each frame and average them to produce the temporal joints profile. The ConvFormer can also be used, for example, to generate temporal joints profiles to reproduce skeletal joint and limb movements of the human subject accurately and smoothly from a 2D input.

Instead of generating queries, keys, and values that represent latent pose representations for individual frames found in typical 3D pose estimators or transformers, the ConvFormer queries skeletal outlines, effectively fusing temporal information and producing temporal joints profile. As described above, a temporal joints profile includes a sequential movement of a specific join in a time and/or motion sequence. Each joint of the skeletal outlines for each frame can be mapped throughout the frames, thereby identifying the sequential movement of each joint by following the movement and location of each joint throughout the frames. The temporal joints profile can be used to analyze a joint's movement in sequence. The plurality of temporal joints profiles can be used to analyze joints' movements in sequence and how they interact in sequence.

In some embodiments, the ConvFormer can also perform a scaled-dot product attention following the fusing of temporal information resulting in the temporal joints profile or the plurality of temporal joints profiles. The ConvFormer's dynamic convolutional multi-headed attention mechanism includes a scaled dot product attention applied for each head of the multi-headed attention mechanism, where the attention can be described as a mapping function that maps a query matrix Q, a key matrix K, and a value matrix V to an output attention matrix. Each head the multi-headed attention mechanism can produce a temporal joints profile or temporal joints profile different from the other heads. For instance, the temporal joints profile(s) produced from different heads can include temporal joints profile(s) produced from different camera angles. In some embodiments, one head can focus on producing a singular temporal joints profile for a singular joint such as a right elbow, while the other heads can focus on producing a singular temporal joints profile for every other joint of the human subject. The ConvFormer can run each head and perform the attentions in parallel in which each attention result is then concatenated, thereby producing a linearly transformed aggregated temporal joints profile in the expected dimension. The resulting aggregated temporal joints profile can include the most accurate and smooth 3D output of a temporal joints profile or temporal joints profile.

In some embodiments, the compute device can also be used to predict body injury. For example, a sensor can continuously record, from a certain angle, a human subject. The recorded video can be sent to the ConvFormer, which can analyze the subject's joint movements. The compute device can use, for example, a machine-learning model and/or algorithm to determine potential body injuries based on the joint movements computed as temporal joints profiles and the frequency of such movements. The compute device can also be used, for example, to determine physical therapy treatments to improve the body (state of health) of a human subject. The compute device can use, for example, a specific temporal joints profiles indicating a healthy bodily movement. For instance, a sensor can record people performing manual labor in which a specific sequence of movements represents a healthy and/or ideal mode of performance. Any significant deviations from this specific sequence can be identified by the sensor capturing data from manual laborers and their joint movements for the compute device to produce a specific physical therapy improvement and/or recommendation to achieve the healthy and/or ideal sequence of movements.

FIG. 1 shows a system block diagram for a compute system to produce a temporal joints profile, according to an embodiment. Compute device 100 can include any processor as described in this disclosure. For instance, the processor can include without limitation a microcontroller, microprocessor, digital signal processor (DSP) and/or system on a chip (SoC) as described in this disclosure. Compute device 100 includes a memory 104 containing instructions for at least a processor 108. Memory 104 of compute device can be, for example, a memory buffer, a random-access memory (RAM), a read-only memory (ROM), a hard drive, a flash drive, a secure digital (SD) memory card, an external hard drive, an erasable programmable read-only memory (EPROM), an embedded multi-time programmable (MTP) memory, an embedded multi-media card (eMMC), a universal flash storage (UFS) device, and/or the like. Memory 104 can store, for example, video data, image data, fitness data, medical record data, and/or the like. Memory 104 can further store, for example, one or more machine learning models, and/or code that includes instructions to cause processor 108 to execute one or more processes or functions such as, but not limited to, a data preprocessor, one or more machine-learning models, or the combination thereof.

Compute device 100 can include, for example, a hardware and/or software component to facilitate data communication between compute device 100 and external devices such as, but not limited to, a camera, a sensor, a server, a network, a communication interface, or the combination thereof. Compute device 100 can include, for example a communication interface operatively coupled to and used by processor 108 and/or the memory 104. For example, a communication interface can include a network interface card (NIC), a Wi-Fi® module, a Bluetooth® module, an optical communication module, and/or any other suitable wired, wireless communication interface, or the like thereof. The communication interface can be configured to connect the compute device 100 to a network. In some instances, the communication interface can facilitate receiving and/or transmitting data such as a video data, image data, fitness data, medical record data, or the like thereof as a function of the network.

Compute device 100 also includes a ConvFormer module 12. ConvFormer module can be, for example, a hardware/software module and/or convolutional transformer that leverages a dynamic convolutional multi-headed self-attention mechanism for monocular 3D human pose estimation. For example, ConvFormer module 124 can include a spatial-temporal convolutional transformer. Compute device 100 also includes processor 108, which contains and/or can access (e.g., from memory 104) instructions to cause compute device 100 and/or ConvFormer module 124 to receive, from a sensor 116, a video input containing image frames 120 representing a subject 112. In some instances, the image frames 120 can contain a measured temporal joint data of subject 112 across at least two frames of image data from sensor 116. For example, the measured temporal joint data can include the dimensional location of a recognizable human subject as the location shifts following the movements of the human subject captured across multiple image frames. In some cases, the temporal joint data can include a rectangular outline and/or overlay surrounding the human subject as well as 2D coordinates of the corners of the outline and/or overlay.

Sensor 116 can be, for example, a device used to capture a physical phenomenon and output an electrical signal. For example, sensor 116 can include any one or more of a video camera, an image sensor, motion sensor, thermal sensor, biochemical sensor, pressure sensor, or the like thereof. Sensor 116 can include multiple sensors where each sensor is housed with each other in a sensor case, forming a sensor suite. A subject 112 can be, for example, a recognizable moving human captured by sensor 116 and/or within the video input. Subject 112 can include, for example, a central figure in the video input. In some instances, subject 112 can include multiple subjects, where each subject is identified by sensor 116 and/or compute device 100. A "video input," as used in this disclosure, can be for example an electronic input containing electronic signals of a 2D visual media. The video input can be embodied in any electronic medium for recording, copying, playback, broadcasting, displaying, or the like thereof. The video input can include image frames 120. An "image frame," as used in this disclosure, can be, for example, an image in a sequence of images forming a video. For example, a video input having 60 frames per second can include 60 image frames for one second of video input. A video input of a human person performing manual labor can be multiple image frames where each image frame contains an image of a pose the human subject is making while performing the manual labor. The multiple image frames can include, for example, a sequence of such pose and/or manual labor. The video input can include, for example, a recorded 2D visual media of subject 112 and its movements from a fixed position via placement of sensor 116.

Memory 104 stores instructions to cause processor 108 to identify, via ConvFormer module 124, multiple joints from subject 112. A "joint" is for example a connection point between two or more limbs and/or bones. In some implementations, compute device 100 can denote a joint as a circular dot placed on top of each image frame 120 where a joint within an image frame is located. ConvFormer module 124 is further configured to identify multiple joints using a spatial joint machine-learning model 128. A "spatial joint machine-learning model" can be, for example, any machine-learning model and/or algorithm used to output multiple joint localization overlays. Spatial joint machine-learning model 128 can be consistent with any machine-learning model as described herein. A machine-learning model can include any supervised and/or unsupervised machine-learning model. A machine-learning model can enable deep learning. In some implementations, compute device 100 can use convolutional neural networks (CNNs) for image processing and object detection. In another implementations, ConvFormer module 124 can employ recurrent neural networks (RNNs) to enable the algorithms of a machine-learning model to teach itself to identify joints, limbs, 3D skeletal representations, and the like thereof. In another example, compute device 100 can use a feed-forward neural network and multiple hidden layers used to transform the video input and its image frames 120 into recognizable 3D frame interrelations 136. The feed-forward neural network and hidden layers can also be used to identify multiple joints of subject 112 and/or compute 2D joint localizations from the video input and/or image frames 120. The feed-forward neural network and hidden layers can also be used to identify limb segments and/or compute 2D segmental localizations.

Memory 104 stores instructions to cause processor 108 to train, via ConvFormer module 124, spatial joint machine-learning model 128 using a spatial joints training set. A "spatial joints training set" can be, for example, any training data containing a two-dimensional human pose correlated to a two-dimensional joints profile. Processor 108 can be further instructed to retrieve any training set from a database. Processor 108 can be further instructed to record and retrieve any inputs and outputs for any machine-learning model in the database. In some implementations, the database can be a cloud database where compute device 100 is connected via a network interface to access the cloud database. Memory 104 stores instructions to cause processor 108 to train, via ConvFormer module 124, spatial joint machine-learning model 128 with the spatial joints training set and execute spatial joint machine-learning model 128 with image frames 120 as an input to output the multiple joint localization overlays. A "joint localization overlay," is, for example, a 2D map of joints on an image. For example, the 2D joint localization can include an image of circular dots placed on top of each image frame 120, where each circular dot denotes a joint of a human subject 112. ConvFormer module 124 can produce a joint localization overlay for each individual frame of image frames 120.

Memory 104 stores further instructions to cause processor 108 to determine, via ConvFormer module 124, multiple frame interrelations based on the joint localization overlay using a limb segment machine-learning model 132. A "limb segment machine-learning model" is, for example, any machine-learning model used to output frame interrelation 136. A "frame interrelation" is, for example, a frame-wise relation and/or sequence between two or more frames, where the frame-wise relation identifies limb segments connecting multiple joints from a joint localization over. In some implementations, frame interrelations 136 can incorporate limb segments to be included in the joint localization overlay, thereby creating a comprehensive skeletal outline of joints and limbs. Memory 104 further stores instructions to cause processor 108 to train via ConvFormer module 124 limb segment machine-learning model 132 using an interrelation training set, which can be for example a training set that contains a limb segment image data correlated to a limb matrix in a motion sequence. ConvFormer module 124 then executes limb segment machine-learning model 124 to identify the multiple frame interrelations 136 using the image frames 120 as an input. In some implementations, limb segment machine-learning model 132 can receive the joint localization overlays as an input to train limb segment machine-learning model 132.

Alternatively and additionally, ConvFormer module 124 can include a spatial attention module and a temporal transformer module. The spatial attention module receives image frames 120 of 2D human poses as inputs and extracts a high dimensional feature for each frame's joint correlations as denoted by the 2D segmental localization. The spatial attention module can also extract multiple 2D segmental localizations for each individual frame and globally across a motion of sequence of subject 112 captured in image frames 120. In some implementations, the spatial attention module contains spatial joint machine-learning model 128 and/or limb segment machine-learning model 132 as limb segment machine-learning model 132 outputs the frame interrelations 136, where the frame interrelations 136 include a sequence of spatial blocks denoted by the joint localization overlays. In some implementations, the input for ConvFormer module 124 includes image frames 120 of 2D human poses. For example, an input is a 2D pose with J joints that is represented by two coordinates (u, v). The spatial attention module and/or limb segment machine-learning model 132 maps the coordinate of each joint found in a frame into a high-dimensional feature with a trainable linear layer. Then a learned positional encoding via summation is applied to the high-dimensional feature. Given a sequence of 2D poses $S=\{s_i\}_{i=1}^T \subset \mathbb{R}^{J \times 2}$ where T represents the number of frames in the sequence, 3D skeletal representations can be reconstructed in the joint that is relative to the camera reference frame, where the camera reference frame is where the root joint sits at the origin. For example, given a sequence of poses $\{P_i\}_{i=1}^T \subset \mathbb{R}^{J \times 2}$ and $W \in \mathbb{R}^{2 \times d}$ and $E_{pos} \in \mathbb{R}^{J \times d}$, the spatial attention module and/or limb segment machine-learning model 132 encodes $P_i$ as follows:

$$x_i = P_i W + E_{pos}, \, i \in \{1, \ldots, T\}$$

where d represents the dimension of the embedding. Subsequently, the spatial feature sequence $\{x_i\} \subset \mathbb{R}^{J \times d}$ is fed into the spatial attention module of ConvFormer module 124, which applies a spatial attention mechanism with respect to the joint dimension to integrate information across the complete pose. The output for the i-th frame of the b-th spatial attention module of ConvFormer module 124 is denoted by $z_i^b \in \mathbb{R}^{J \times d}$.

Memory 104 can further instruct processor 108 to compute, via ConvFormer module 124, a 3D pose sequence based on the frame interrelations 136. A "3D pose sequence" can be, for example, a sequence of 3D frames where each 3D frame corresponds to a 2D frame of the image frames 120. In other words, ConvFormer module 124 can convert a 2D frame into a 3D frame. In some implementations, ConvFormer module 124 can use a CNN to produce the 3D pose sequence. In another implementation, ConvFormer module 124 can also extract multiple scaled frame interrelations based on a convolutional filter size prior to generating the temporal joints profile. A "convolutional filter size" can be, for example, a 2D kernel size for which convolutional layers are to follow. The convolutional filter size can be used to adjust the level of sparsity to be applied for the frame interrelations 136 denoted by the scaled frame interrelations.

Memory 104 further stores instructions to cause processor 108 to receive, via ConvFormer module 124, the frame interrelations 136 from limb segment machine-learning model 132, train a temporal profile machine-learning model 140 using a temporal sequence training set, and execute temporal profile machine-learning model 140 using the frame interrelations 136 as an input to output a temporal joints profile 144. A "temporal joints profile machine-learning model" can be, for example, any machine-learning model and/or algorithm used to output a temporal joints profile. A "temporal sequence training set" can be, for example, a training set that contains a temporal pose sequence correlated to a temporal joint sequence. A "temporal joints profile" can be, for example, a sequence of a joint from 3D poses by a human subject given a video input. In some implementations, temporal joints profile 144 can include a graphical indicator of a joint based on the frame interrelations 136 and/or 3D pose sequence. For example, the frame interrelations 136 can include a 3D sequence of a human subject's skeletal representation. Temporal joints profile 144 can include a line following the specific movement of a specific joint from 3D frame interrelations, identifying a fluid temporal motion of that specific joint. In some implementations, ConvFormer module 124 can enable temporal profile machine-learning model 140 to produce multiple temporal joints profiles for each joint of a joint localization overlay, where each joint represents the corresponding joint of a human subject captured by the image frames. In some implementations, temporal profile model 140 can include deep learning. For example, using a neural network, temporal profile machine-learning model 140 can structure algorithms in hidden layers that map each joint and limb segment of a human body through the hidden layers to produce temporal joints profile 144 and/or multiple temporal joints profiles.

Temporal joints profile 144 can vary, for example, based on a temporal window. A "temporal window" can be, for example, a finite window of time of a video stream. For instance, a video stream with a duration of 1 hour can be inputted into ConvFormer module 124. The video stream can include a human subject performing a variety of manual labor and body movements. ConvFormer module 124 can analyze the movements of a specific window of that duration based on the temporal window. The temporal window can include, for example, a time window of the last 5 minutes of the inputted video stream. This is so, at least in part, for ConvFormer module 124 to parse temporal joints profile 144 of an entire sequence of the video input into smaller chunks.

Processor 108 can be instructed to determine an injury risk datum 152 and a physical therapy improvement 148 based on temporal joints profile 144. An "injury risk datum" can be, for example, any readable information describing a bodily injury or harm that is present in a human subject based on the human subject's 3D skeletal representation or temporal joints profile(s). In some implementations, injury risk datum 152 can include information about potential injury risks that can develop based on temporal joints profile 144. For example, a human subject captured by a camera can be mapped by ConvFormer 124 to a 3D skeletal representation, which can be denoted by temporal joints profile 144, can indicate, based on that the human subject's movements, of present bodily injury and/or potential bodily injury. A "physical therapy improvement" can be, for example, a physical improvement plan used to rehabilitate a human subject suffering from an identified bodily injury or potential injury based on the human subject's 3D temporal joints profile.

Figure 2:
FIG. 2 is a flow diagram illustrating an embodiment of a dynamic convolutional multi-headed attention for estimating a human pose, according to an embodiment.

FIG. 2 is a flow diagram illustrating an embodiment of a method 200 for dynamic multi-headed convolutional attention for estimating a human pose. At 205, method 200 includes receiving, from a sensor operatively coupled to a compute device, image frames containing a measured temporal joint data of a subject across at least two frames of image data from the sensor. In some implementations, method 200 can include receiving, from multiple sensors, multiple video inputs, each sensor pointing to the at least a subject from a different angle.

In some implementations, method 200 can include causing the processor of non-transitory, processor-readable medium to receive the image frames as an input, train a spatial joint machine-learning model of multiple machine-learning models using a spatial joints training set containing a two-dimensional human pose correlated to a two-dimensional joints profile, and execute the spatial joint machine-learning model using the image frame as an input, the spatial joint machine-learning model outputs multiple joint localization overlays.

At 210, method 200 includes computing multiple averaged convoluted quantitative identifiers based on the plurality of image frames. In a non-limiting embodiment, method 200 can include computing multiple convoluted quantitative identifiers such as queries, keys, and values. Method 200 can further include causing the processor to extract multiple scaled frame interrelations based on a convolutional filter size.

In some implementations, method 200 can include, prior to training a multi-headed temporal profile machine-learning model, receiving the plurality of joint localization overlay from the spatial joint machine-learning model, training the limb segment machine-learning model using an interrelation training set that contains a limb segment image data correlated to a limb matrix in a motion sequence, and executing the limb segment machine-learning model using the plurality of joint localization overlays as an input, where the limb segment machine-learning model outputs multiple frame interrelations. For instance, the limb segment machine-learning model uses the plurality of joint localization overlays from the spatial join machine-learning model to produce a completed 2D overlay identifying joints and limbs of a human subject.

In some implementations, method 200 can also include receiving the plurality of frame interrelations from the limb segment machine-learning model, training a temporal profile machine-learning model of the plurality of machine-learning models using a temporal sequence training set containing a temporal pose sequence correlated to a temporal joint sequence, and executing the temporal profile machine-learning model using the plurality of frame interrelations as an input, the temporal profile machine-learning model outputs a temporal joints profile. The temporal profile machine-learning model can produce a temporal joints profile and/or temporal joints profile within each head of a multi-headed attention process, prior to the attention and the concatenation of each head of a transformer with a dynamic multi-headed convolutional attention mechanism.

At 215, method 200 includes training the multi-headed temporal profile machine-learning model of multiple machine-learning models using a temporal joints training set that includes a concatenated temporal profile correlated to a concatenated temporal sequence. In some implementations, training the temporal profile machine-learning model and/or training any machine-learning model can include deep learning.

At 220, method 200 includes executing the multi-headed temporal profile machine-learning model to output multiple temporal joints interrelations using the plurality of averaged convoluted quantitative identifiers as an input. In some implementations, the plurality of averaged quantitative identifiers forms a temporal joints profile and/or multiple temporal joints profile, where the averaged quantitative identifiers are computed as a result of convolution. For instance, method 200 can also include generating multiple frame interrelations based on the averaged convolutional quantitative identifiers, and reducing sparsity of multiple joint interrelations between the plurality of frame interrelations temporal joints model using the plurality of averaged convoluted quantitative identifiers.

At 225, method 200 includes generating an aggregated temporal joints profile based on the plurality of temporal joints interrelations. The aggregated temporal joints profile can include multiple temporal joints profiles that underwent a scaled dot product attention and concatenated to produce the aggregated temporal joints profile. In some implementations, method 200 can include computing the plurality of averaged convoluted quantitative identifiers and generating the aggregated temporal joints profile simultaneously.

Figure 3:
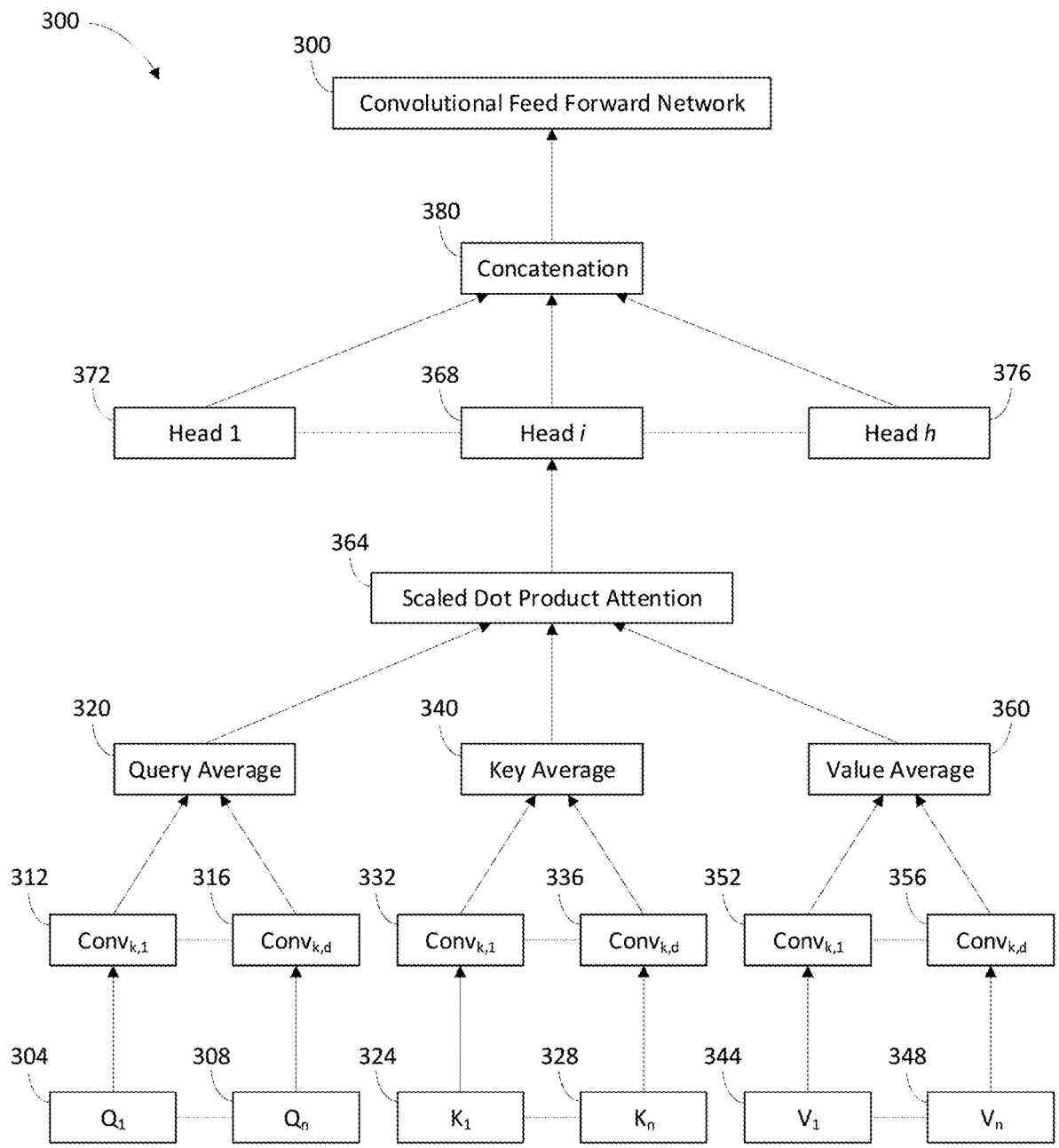
FIG. 3 is a block diagram of an embodiment of a dynamic convolutional multi-headed attention for estimating a human pose, according to an embodiment.

FIG. 3 is a block diagram of an embodiment of a dynamic multi-headed convolutional attention mechanism 300 of the ConvFormer for estimating a human pose. The ConvFormer for estimating a human pose can be consistent with the ConvFormer module described in further detail above. In typical multi-headed attention mechanisms, queries, keys, and values are generated via convolutions with weights of the following dimension (T, T, k) where k is the kernel size and the 1D convolutions have depth the size of input sequence. In one or more implementations, the ConvFormer's dynamic multi-headed convolutional attention mechanism fuses the temporal evolution of a patch of deep joint features in one shot, which is distinct from typical temporal attentions, which attends complete pose encoding throughout the motion sequence. Dynamic multi-headed convolutional attention mechanism 300 includes queries, keys and values that undergo convolution to produce averaged convoluted quantitative identifiers such as query average 320, key average 340, and value average 360. It is noted that the output from the spatial attention mechanism of the dynamic multi-headed convolutional attention mechanism outputs a sequence $\{z_i^B\}_{i=1,\ldots,T} \subset \mathbb{R}^{J \times d}$ where B is the number of spatial blocks and T is the number of frames in the sequence. In some embodiments, $z_i^k$ can be represented in $\mathbb{R}^{1 \times J \cdot d}$ and thus, the ConvFormer can concatenate these features along a first axis, resulting in:

$$X_0 = \text{Concatenate}(z_1^B, \ldots, z_T^B) \in \mathbb{R}^{T \times J \cdot d}$$

Following this procedure the dynamic multi-headed convolutional attention mechanism incorporates a learned temporal embedding to deep joint features evolution throughout time, such that $E_{temp} \in \mathbb{R}^{J \times J \cdot d}$ and $X = X_0 + E_{temp}$ are the inputs into the temporal attention mechanism of the ConvFormer as described in FIG. 1. As the dynamic multi-headed convolutional attention mechanism follows a many-to-one prediction scheme, the dynamic multi-headed convolutional attention mechanism down samples the spatial axis with a linear projection and then perform a temporal convolution with one output channel such as $p = \text{Conv}_{T,1}(Z^B W)$ where $W \in \mathbb{R}^{J \cdot d \times J}$ and $\text{Conv}_{T,1}$ denotes a temporal convolution with one output channel and T inputs. To train this network, the dynamic multi-headed convolutional attention mechanism applies a Mean Per Joint Position Error (MPJPE) loss to minimize the error during optimization, where the loss function is defined as:

$$L(p, \hat{p}) = \frac{1}{J}\sum_{i=1}^{J}\|p_i - \hat{p}_i\|_2$$

where p is the ground truth 3D pose and $\hat{p}$ is the predicted pose and i is indexing specific joints in a skeleton.

Instead of generating queries, keys, and values, which represent latent pose representations for individual frames found in typical 3D pose estimators or transformers, the dynamic multi-headed convolutional attention mechanism queries skeletal outlines, effectively fusing temporal information and producing temporal joints profile. Convolutional Scaled Dot Product Attention 364 can be described as a mapping function that maps a query matrix Q of Query Average 320, a key matrix K of Key Average 340, and a value matrix V of Value Average 360 to an output attention matrix where the output attention matrix entries are scores representing the strength of correlation between any two elements in the axis being attended. The output of Convolutional Scaled Dot Product Attention 364 can be expressed as:

$$\text{Attention}(Q,K,V)=\text{Softmax}(QK^T/\sqrt{d})V$$

The query, keys, and values are computed in the same manner for a fixed filter length. The feature aggregation method to produce aggregated temporal joints profile 380 can be expressed as:

$$Q = \text{Conv}_{k,c_{out}}(z) = \sum_{i=1}^{d_{in}} \sum_{k=1}^{K} w_{d_{out},i,k} \cdot z_{t,i-\frac{k-1}{2}+k}$$

Here, k denotes the kernel size, $c_{out}$ denotes the output filter, $d_{out}$ denotes output dimension. This is juxtaposed against a classic scaled dot product attention where queries, keys, and values are generated via a linear projection which provides global scope and redundancy due to the complete connectivity. The dynamic multi-headed convolutional attention mechanism 300 introduces sparsity via convolutions to decrease connectivity while simultaneously fusing complete temporal information prior to Convolutional Scaled Dot Product Attention 364. Moreover, due to the feature aggregation method of the dynamic multi-headed convolutional attention mechanism, the dynamic multi-headed convolutional attention mechanism provides context at different scales. Moreover, due to the convolution mechanism of the dynamic multi-headed convolutional attention mechanism, the dynamic multi-headed convolutional attention mechanism queries on inter-frame level where the temporal joints profile is learned. To this end, the dynamic multi-headed convolutional attention mechanism can use n convolutional filter sizes to extract different local contexts at scales $\{k_i\}_{i=1}^{n}$ and then perform an averaging operation to generate the query, keys, and values that attention is applied to, for each head:

$$Q = \text{Concat}(Q_1, \ldots, Q_n)\eta_Q = \sum_{i=1}^{n}\eta_Q(i)Q_i \quad \text{where} \quad \sum_{i=1}^{n}\eta_Q(i) = 1$$

$$K = \text{Concat}(K_1, \ldots, K_n)\eta_K = \sum_{i=1}^{n}\eta_K(i)K_i \quad \text{where} \quad \sum_{i=1}^{n}\eta_K(i) = 1$$

$$V = \text{Concat}(V_1, \ldots, V_n)\eta_V = \sum_{i=1}^{n}\eta_V(i)V_i \quad \text{where} \quad \sum_{i=1}^{n}\eta_V(i) = 1$$

where n is the number of convolution filters used, $\eta_Q$, $\eta_K$, $\eta_V \in \mathbb{R}^{n \times 1}$ and $Q_i$, $K_i$, and $V_i$ are generated as above. As shown in FIG. 3, the first convolution filters for $Q_1$, $K_1$, and $V_i$ are depicted with reference labels 304, 324, and 344, respectively, while, depending on the number of convolution filters, the last convolutional filters for $Q_1$, $K_1$, and $V_1$ are found with reference labels 308, 328, and 348 respectively. As described above, k denotes the kernel size, $c_{out}$ denotes the output filter, therefore, as shown in FIG. 3, the convolutional equations for $Q_1$, $K_1$, and $V_1$ are depicted with reference labels 312, 332, and 352, respectively, while the convolutional equations for $Q_n$, $K_n$, and $V_n$ are depicted with reference labels 316, 332, and 356, respectively.

Multi-headed Dynamic Convolutional Attention (MDCA) leverages multiple heads (e.g., heads 372, 368 and 376) to jointly model information from multiple representation spaces. As shown in FIG. 3, each head 372, 368, 376 applies Convolutional Scaled Dot Product Attention 364 in parallel. The output of the MDCA is the concatenation of each head 372, 368, 376 and its attention outputs, where the concatenated result is the aggregated temporal joints profile 380. The concatenated result is then fed into a feed-forward network such as convolutional feed forward network 385 and can be expressed as: MDCA(Q,K,V)=Concatenate $(H_1, \ldots, H_h)$ where $H_i = \text{Attention}(Q_i, K_i, V_i) \in \{1, \ldots, h\}$ where $Q_i$, $K_i$, and $V_i$ are computed via the procedure defined above. Lastly, the ConvFormer can be defined as:

$$X_b' = \text{NDCA}(\text{LN}(X_{b-1})) + X_{b-1}, b=1, \ldots, B$$

$$X_b = \text{FFN}(\text{LN}(X_b^i)) + X_b^i, b=1, \ldots, B$$

where LN(•) denotes layer normalization and FFN denotes a feed forward network. As described previously above, the ConvFormer module of FIG. 1 can contain two mechanisms such as the spatial attention mechanism and the temporal attention mechanism. Both the spatial and temporal attention mechanisms of the ConvFormer module have B identical blocks. The output of the spatial ConvFormer encoder such as the spatial attention mechanism as described in FIG. 1 is $Y \in R T \times J \times d$ where T is the frame sequence length, J is the number of joints, and d is the embedding dimension. Additionally, the output of the temporal ConvFormer such as the temporal attention mechanism as described in FIG. 1 is $Y \in R T \times Jd$.

Figure 4:
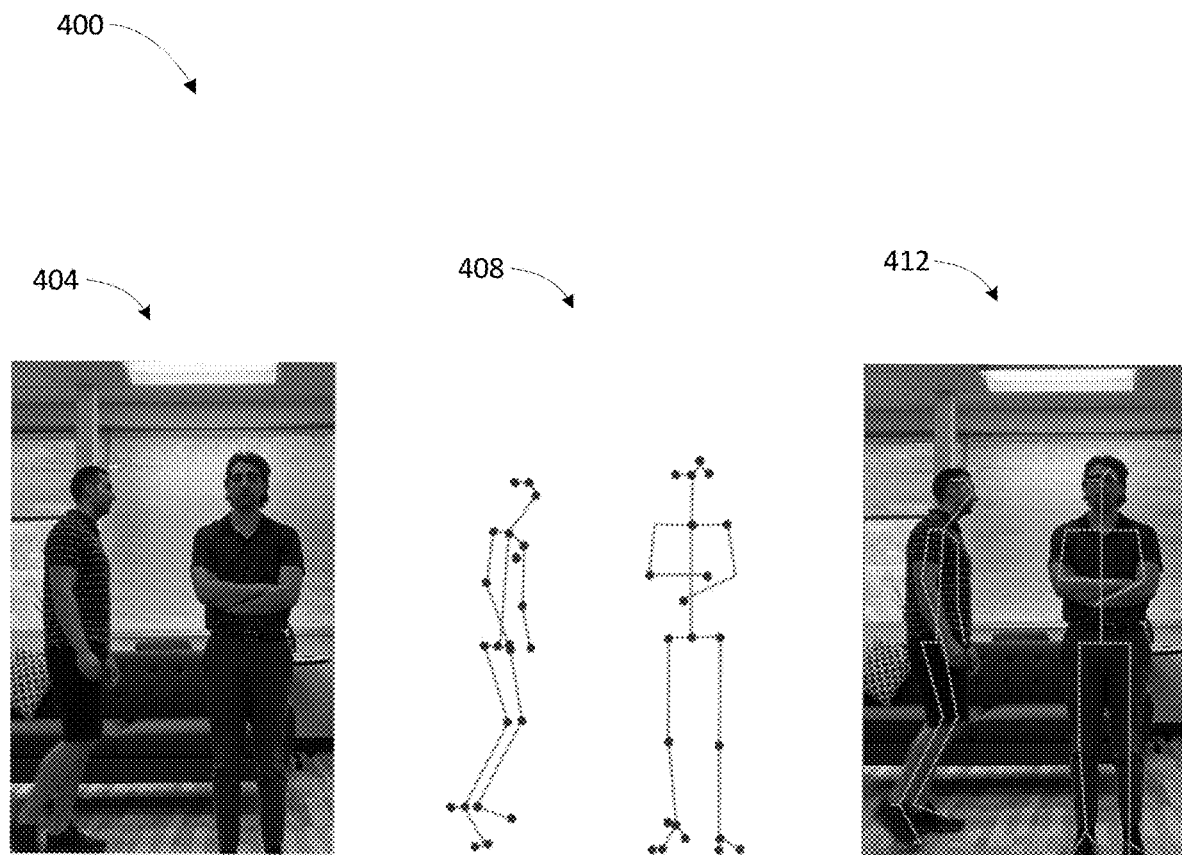
FIG. 4 is a schematic illustration of a method for estimating a set of poses, according to an embodiment.

FIG. 4 shows a schematic illustration of a method for estimating a set of poses, according to an embodiment. FIG. 4 illustrates a process 400 of receiving image frames of human subjects, identifying the joints and limbs of the human subjects, and producing a 2D skeletal outline and/or overlay based on the joints and limbs. The image at reference label 404 depicts an unfiltered image frame containing two human subjects. The image at reference label 408 depicts a schematic 2D skeletal representation of each human subject's joints and limbs combinations. The image at reference label 412 depicts the 2D skeletal representation overlayed on top of the original unfiltered image frame 404. The ConvFormer module of FIG. 1 can use a spatial joint machine-learning model and/or a limb segment machine-learning model to generate a set of joints, a set of limbs, and a pose estimation for each subject from multiple subjects in an image recorded by a sensor.

Figure 5:
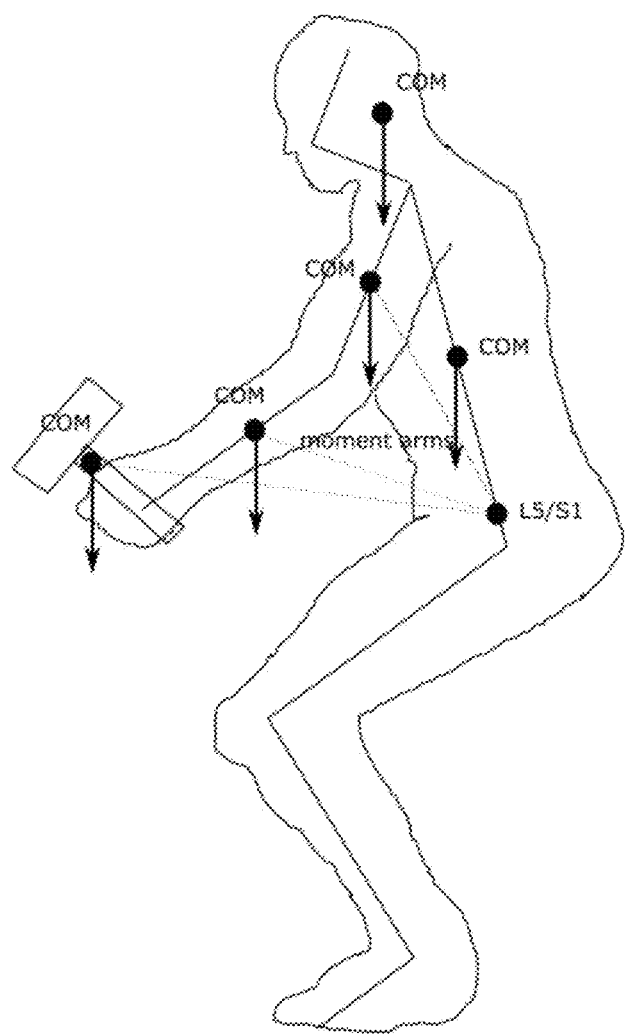
FIG. 5 schematic illustration of determining static load on a joint from an image frame to determine risk of injury and physical therapy improvement, according to an embodiment.

FIG. 5 shows a schematic illustration of determining static load on a joint from an image frame to determine risk of injury and physical therapy improvement, according to an embodiment. As a result of the ConvFormer module generating a temporal joints profile or multiple temporal joints profile, the ConvFormer can also identify the torque delivered around multiple joints, which can be used to further identify bodily injury, potential risk, and some physical therapy improvement plan to alleviate the bodily injury or risk. A joint torque can refer to a total torque delivered around a joint, usually delivered by muscles. For each joint from a set of joint in a body of a subject (e.g., a patient, a worker, an athlete, etc.), multiple body parts can often contribute to a torque of force about the joint. The sum of all such torques can yield a total joint torque, which can be viewed as a rotational force about the joint. As shown in FIG. 5, a dynamic load model for the back joint (L5/S1 joint) can be computed by a method as described herein. The method, however, can be similarly applied to any of the other joints of the subject. A total dynamic load on the back joint can be the sum of the torques caused by weight, linear acceleration, and angular acceleration of the body segments above the L5/S1 joint.

A weighted torque of the L5/S1 joint can be computed by a sum of all weighted torques of body parts and objects weighted above the back. Those can include the head, the torso, the arms, the hands, or an object(s) in the hands. The weighted torque of a body part can be given by:

$$W = m \times g \times r$$

where m is the mass value of the body part or the object(s), g is the gravitational constant, and r the distance between the center of mass (COM) of the segment and the L5/S1 in the horizontal plane. The COM, the percentage of total body weight, and the radius of gyration for each body part or the object(s) can be modeled, for example, after data sets obtained from exact calculations made on cadaver bodies. The subjects' total mass can be given by the user or can be estimated using a 3D representation of a skeleton (as described with respect to FIG. 1) in conjunction with an auxiliary neural network that can predict the subject's Body Mass Index (MBI) and/or weight based on facial features of the subject and/or the 3D representation of the skeleton.

A total linear inertial torque is the sum of linear inertial torques of all body parts and any auxiliary objects interacting with the joint of interest (L5/S1 joint). The 3D reconstruction is formatted so that the vertical direction contains all information used to compute the linear force due to movement. The linear inertial torque can be computed using:

$$L = r \times m \times a_2$$

where r is the torque arm, m is the mass value of the body part or object, and $a_2$ denotes a vertical acceleration of the COM of a body part (e.g. head, torso, arms, hands, or object in the hands). The linear inertial torque can be computed for each image/frame from the 3D representation of the skeleton using a central difference method of differentiation. The linear inertial torque can be filtered to remove noise without changing characteristics of the image/frame using a double pass Butterworth filter whose cutoff frequency is obtained by applying Jackson's algorithm described above.

A total angular inertial torque is the sum of the angular inertial torques of all body parts and any auxiliary objects interacting with the back. The angular inertial torque for each body part can be computed using:

$$A = m \times \rho^2 \times \alpha$$

where m is a mass of the body part, $\rho$ is a radius of gyration, and $\alpha$ is an angular acceleration. The angle of interest here is the segment angle between the body part and the transverse plane. The acceleration of this angle can be computed and filtered using the same techniques described above for the linear inertial torque. Finally, the total torque about the joint of interest (L5/S1 joint) can be computed as:

$$T = W + L + A$$

Setting all acceleration equal to zero in the above equations, can yield the static torque.

It should be understood that the disclosed embodiments are not intended to be exhaustive, and functional, logical, operational, organizational, structural and/or topological modifications may be made without departing from the scope of the disclosure. As such, all examples and/or embodiments are deemed to be non-limiting throughout this disclosure.

All definitions, as defined and used herein, should be understood to control over dictionary definitions, definitions in documents incorporated by reference, and/or ordinary meanings of the defined terms.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using Python, Java, JavaScript, C++, and/or other programming languages and development tools. Additional examples of computer code include, but are not limited to, control signals, encrypted code, and compressed code.

The drawings primarily are for illustrative purposes and are not intended to limit the scope of the subject matter described herein. The drawings are not necessarily to scale; in some instances, various aspects of the subject matter disclosed herein can be shown exaggerated or enlarged in the drawings to facilitate an understanding of different features. In the drawings, like reference characters generally refer to like features (e.g., functionally similar and/or structurally similar elements).

The acts performed as part of a disclosed method(s) can be ordered in any suitable way. Accordingly, embodiments can be constructed in which processes or steps are executed in an order different than illustrated, which can include performing some steps or processes simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a processor, a field programmable gate array (FPGA), and/or an application specific integrated circuit (ASIC). Software modules (executed on hardware) can include instructions stored in a memory that is operably coupled to a processor, and can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

The invention claimed is:

1. An apparatus, comprising:
at least a processor; and
a memory operatively coupled to the processor, the memory storing instructions that when executed cause the processor to:
receive a plurality of image frames, each image frame from the plurality of image frames containing a measured temporal joint data of a subject;
train a limb segment machine-learning model of a plurality of machine-learning models using an inter-relation training set that contains a limb segment image data correlated to a limb matrix in a motion sequence;
execute the limb segment machine-learning model to identify a plurality of frame interrelations using the plurality of image frames as an input; and
generate a temporal joints profile based on the plurality of frame interrelation.

2. The apparatus of claim 1, wherein the instruction to cause the processor to generate the temporal joints profile is based on a plurality of video inputs from a plurality of sensors pointing at the subject from different angles, the plurality of sensors including the sensor.

3. The apparatus of claim 1, wherein the memory further stores instructions that when executed, causes the processor to extract a plurality of scaled frame interrelations based on a convolutional filter size prior to generating the temporal joints profile.

4. The apparatus of claim 1, wherein the memory further stores instructions to cause the processor to independently generate a plurality of temporal joints profiles for a plurality of subjects captured by the sensor.

5. The apparatus of claim 1, wherein prior to the memory configures the processor to train the limb segment machine-learning model, the memory further stores instructions to cause the processor to:
   receive the plurality of image frames from a plurality of sensors;
   train a spatial joint machine-learning model of the plurality of machine-learning models using a spatial joints training set containing a two-dimensional human pose correlated to a two-dimensional joints profile; and
   execute the spatial joint machine-learning model using the image frame as an input, the spatial joint machine-learning model outputs a plurality of joint localization overlays.

6. The apparatus of claim 5, wherein the memory further stores instructions to cause the processor to:
   receive the joint localization overlay from the spatial joint machine-learning model;
   train the limb segment machine-learning model using the interrelation training set; and
   execute the limb segment machine-learning model using the plurality of joint localization overlays as an input, the limb segment machine-learning model outputs the plurality of frame interrelations.

7. The apparatus of claim 6, wherein the memory further stores instructions to cause the processor to:
   receive the plurality of frame interrelations from the limb segment machine-learning model;
   train a temporal profile machine-learning model of the plurality of machine-learning models using a temporal sequence training set containing a temporal pose sequence correlated to a temporal joint sequence; and
   execute the temporal profile machine-learning model using the plurality of frame interrelations as an input, the temporal profile machine-learning model outputs the temporal joints profile.

8. The apparatus of claim 1, wherein the plurality of machine-learning model includes deep learning.

9. The apparatus of claim 1, wherein the memory further stores instructions to cause the processor to determine an injury risk datum based on the temporal joints profile.

10. The apparatus of claim 1, wherein the memory further stores instructions to cause the processor to determine a physical therapy improvement based on the temporal joints profile.

11. A non-transitory, processor-readable medium storing processor-executable instructions to cause the processor to:
   receive, from a sensor operatively coupled to the processor, a plurality of image frames containing a measured temporal joint data of a subject across at least two frames of image data from the sensor;
   compute a plurality of averaged convoluted quantitative identifiers based on the plurality of image frames;
   train a multi-headed temporal profile machine-learning model of a plurality of machine-learning models using a temporal joints training set that includes a concatenated temporal profile correlated to a concatenated temporal sequence;
   execute the multi-headed temporal profile machine-learning model to output a plurality of temporal joints interrelations using the plurality of averaged convoluted quantitative identifiers as an input; and
   generate an aggregated temporal joints profile based on the temporal joints interrelations.

12. The non-transitory, processor-readable medium of claim 11, the non-transitory, processor-readable medium further causing the processor to receive, from a plurality of sensors, a plurality of video inputs, each sensor pointing to the at least a subject from a different angle.

13. The non-transitory, processor-readable medium of claim 11, the non-transitory, processor-readable medium further causing the processor to extract a plurality of scaled frame interrelations based on a convolutional filter size prior.

14. The non-transitory, processor-readable medium of claim 11, wherein the non-transitory, processor-readable medium further stores instructions to cause the processor to compute the plurality of averaged convoluted quantitative identifiers and generate the aggregated temporal joints profile simultaneously.

15. The non-transitory, processor-readable medium of claim 11, wherein the non-transitory, processor-readable medium further stores instructions to cause the processor to:
   generate a plurality of frame interrelations based on the averaged convolutional quantitative identifiers; and
   reduce sparsity of a plurality of joint interrelations between the plurality of frame interrelations temporal joints model using the plurality of averaged convoluted quantitative identifiers.

16. The non-transitory, processor-readable medium of claim 11, wherein the non-transitory, processor-readable medium further stores instructions to cause the processor to map the plurality of averaged convoluted quantitative identifiers to an output attention matrix of a plurality of output attention matrices, each output attention matrix representing a sequential pose prior to generating the aggregated temporal joints profile.

17. The non-transitory, processor-readable medium of claim 11, wherein the non-transitory, processor-readable medium further causing the processor to:
   train a spatial joint machine-learning model of the plurality of machine-learning models using a spatial joints training set containing a two-dimensional human pose correlated to a two-dimensional joints profile; and
   execute the spatial joint machine-learning model using the image frame as an input, the spatial joint machine-learning model outputs a plurality of joint localization overlays.

18. The non-transitory, processor-readable medium of claim 17, the non-transitory, processor-readable medium further causing the processor to:
   receive the plurality of joint localization overlay from the spatial joint machine-learning model;
   train the limb segment machine-learning model using an interrelation training set that contains a limb segment image data correlated to a limb matrix in a motion sequence; and
   execute the limb segment machine-learning model using the plurality of joint localization overlays as an input, the limb segment machine-learning model outputs the plurality of frame interrelations.

19. The non-transitory, processor-readable medium of claim 18, the non-transitory, processor-readable medium further causing the processor to:
   receive the plurality of frame interrelations from the limb segment machine-learning model;
   train a temporal profile machine-learning model of the plurality of machine-learning models using a temporal sequence training set containing a temporal pose sequence correlated to a temporal joint sequence; and execute the temporal profile machine-learning model using the plurality of frame interrelations as an input, the temporal profile machine-learning model outputs a temporal joints profile.

20. The non-transitory, processor-readable medium of claim 11, the non-transitory, processor-readable medium further causing the processor to determine an injury risk datum based on the plurality of temporal joints profiles and a physical therapy improvement based on the temporal joints profile.

* * * * *

UNITED STATES PATENT AND TRADEMARK OFFICE
CERTIFICATE OF CORRECTION

PATENT NO. : 11,482,048 B1  
APPLICATION NO. : 17/740650  
DATED : October 25, 2022  
INVENTOR(S) : Alec Diaz-Arias et al.

Page 1 of 1

It is certified that error appears in the above-identified patent and that said Letters Patent is hereby corrected as shown below:

On the Title Page

Column 1, (72) Inventors: "Aiec Diaz-Arias, Columbia, MO (US);" should read -- Alec Diaz-Arias, Columbia, MO (US); --

Signed and Sealed this  
Twenty-fifth Day of July, 2023

Katherine Kelly Vidal  
*Director of the United States Patent and Trademark Office*